United States Patent [19]
Sohma et al.

[11] Patent Number: 6,129,677
[45] Date of Patent: Oct. 10, 2000

[54] NON-INVASIVE HEART MONITORING APPARATUS AND METHOD

[75] Inventors: Takeshi Sohma; Yoshihiro Sugo; Rie Tanaka; Wenxi Chen; Hiromitsu Kasuya; Kohei Ono, all of Tokyo, Japan

[73] Assignee: Nihon Kohden Corporation, Tokyo, Japan

[21] Appl. No.: 09/131,678

[22] Filed: Aug. 10, 1998

[30] Foreign Application Priority Data

Aug. 8, 1997 [JP] Japan ................................. 9-214308

[51] Int. Cl.⁷ .................................................. A61B 5/0452
[52] U.S. Cl. ............................................................. 600/513
[58] Field of Search ............................................. 600/513

[56] References Cited

U.S. PATENT DOCUMENTS

| | | | |
|---|---|---|---|
| 3,734,086 | 5/1973 | Phelps, Sr. ............................ | 600/513 |
| 4,137,910 | 2/1979 | Murphy .................................. | 600/513 |
| 4,425,922 | 1/1984 | Conti et al. ........................... | 600/513 |

*Primary Examiner*—William E. Kamm
*Attorney, Agent, or Firm*—Sughrue, Mion, Zinn, Macpeak & Seas, PLLC

[57] ABSTRACT

An apparatus for non-invasion heart monitoring includes electrocardiogram measuring means (1) for measuring electrocardiograms, pulse wave measuring means (2) for measuring pulse waves, and a CPU (30) for processing electrocardiogram signals derived from the electrocardiogram measuring means (1) and pulse wave signals derived from the pulse-wave measuring means (2). The CPU (30) detects the amplitudes of the pulse waves corresponding to the R waves of the cardiogram and the pulse wave propagation times, and computes a ratio (Nr/N) of the heart rate N and the heart rate Nr exclusive of the heart beats of wave deficits.

12 Claims, 3 Drawing Sheets

NON-INVASIVE HEART MONITORING APPARATUS AND METHOD

BACKGROUND OF THE INVENTION

1. Field of the Invention

The present invention relates to an apparatus for noninvasively monitoring changes in the heart contractions of the heart by use of electrocardiogram information and pulse wave information.

2. Related Art

The non-invasive monitoring apparatus uses mainly the information of electrocardiograms, arterial oxygen saturation, blood pressure measured by the oscillometric blood-pressure measuring apparatus and the like as parameters representative of dynamic states of a patient. Of those parameters, electrocardiogram information, arterial oxygen saturation and the like may continuously be measured. In particular the electrocardiogram information is used as a parameter sensitively representing a change of a dynamic state of the patient.

Thus, the electrocardiogram information has been used as the continuously monitoring parameter. An arrhythmia of the patient is monitored by use of the waveforms and heart rates on the electrocardiogram. The monitoring based on only the electrocardiogram has the following problems.

The patient monitoring apparatus can monitor an abnormality, e.g., arrhythmia, of the excitation conducting system, but cannot monitor, for example, a pulse deficit, which arises from an abnormality of the heart contraction. In the case of the pulse deficit, the heart cannot supply sufficient amounts of blood to the peripheries of the internal organs, to possibly cause serious diseases. For this reason, it is necessary to monitor the occurrence of the pulse deficit in a continuous manner. Here, the term "pulse deficit" includes two states, a first state in which the heart propels little amount of blood and a second state in which the ventricle is insufficiently filled with blood and the heart contraction is unsatisfactory.

Where only the electrocardiogram information for the parameter continuously and non-invasively obtained is used, there is a limit in monitoring changes in the heart contractions.

SUMMARY OF THE INVENTION

Accordingly, an object of the present invention is to monitor changes in the heart contractions non-invasively.

In a first aspect of the present invention, there is provided a patient monitoring apparatus comprising: electrocardiogram measuring means for measuring electrocardiograms; pulse wave measuring means for measuring pulse waves; pulse wave data detecting means for detecting at least a pulse wave propagation time by use of electrocardiogram information measured by the electrocardiogram measuring means and pulse wave signals measured by the pulse wave measuring means; and occurrence-frequency detecting means for obtaining data on a frequency of occurrence of pulse wave deficits by use of pulse wave data detected by the pulse wave data detecting means.

In the above-mentioned apparatus, the occurrence-frequency detecting means obtains data on a frequency of occurrence of pulse deficits by use of at least the pulse wave propagation time.

According to the a second aspect of the present invention, the pulse-wave data detecting means detects the amplitudes of pulse waves measured by the pulse-wave measuring means.

In this embodiment the present invention obtains data on a frequency of occurrence of wave deficits by use of at least the pulse pulse propagation time and the amplitude of pulse wave.

DETAILED DESCRIPTION OF THE PREFERRED EMBODIMENTS

An embodiment of the present invention will be described. The embodiment is a patient monitoring apparatus for monitoring changes in the heart contractions. The patient monitoring apparatus is generally made up of an electrocardiogram measuring means 1, a pulse wave measuring means 2 for measuring a pulse wave, a pulse wave data detecting means 3 for detecting at least a pulse wave propagation time by use of a cardiographic waveform measured by the electrocardiogram measuring means 1 and a pulse wave measured by the pulse wave measuring means 2, and an occurrence-frequency detecting means 4 for obtaining data on a frequency of occurrence of pulse deficits on the basis of the pulse wave data detected by the pulse wave data detecting means 3.

Figure 2:
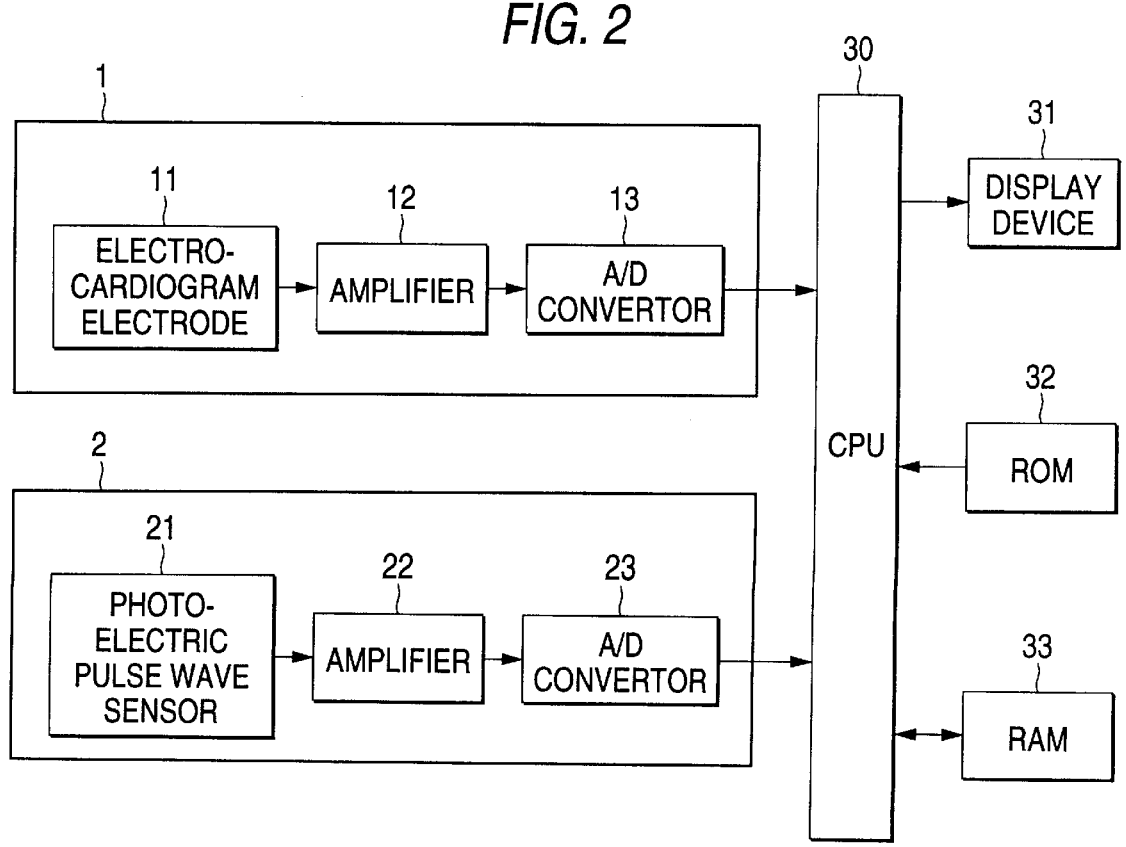
FIG. 2 is a block diagram showing a hardware arrangement of the patient monitoring apparatus of FIG. 1.

An arrangement of the patient monitoring apparatus is shown in detail in FIG. 2. The electrocardiogram measuring means 1 includes an electrocardiogram electrode 11 to be put on the chest of a patient, an amplifier 12 for amplifying a cardiogram signal derived from the electrocardiogram electrode 11, and an A/D converter 13 for converting the amplified cardiogram signal into a digital signal. The pulse-wave measuring means 2 includes a photoelectric pulse wave sensor 21 put on the finger tip of the patient, an amplifier 22 for amplifying a pulse wave signal derived from the photoelectric pulse wave sensor 21, and an A/D converter 23 for the amplified pulse wave signal into a digital signal. The output signals of the A/D converter 13 and the A/D converter 23 are input to a CPU 30.

Figure 3:
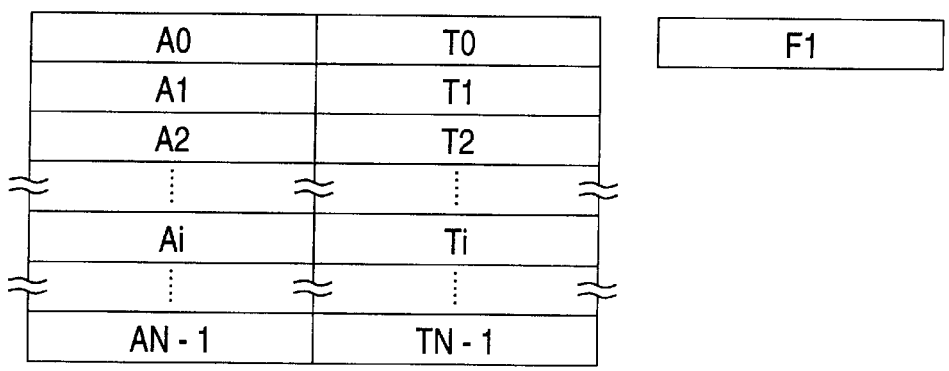
FIG. 3 is a diagram showing the contents of a RAM 33 in the FIG. 2 arrangement.

The CPU 30 is connected to a display device 31, a ROM 32 and a RAM 33. The CPU 30 receives a cardiogram signal from the electrocardiogram measuring means 1 and a pulse wave signal from the pulse wave measuring means 2, processes those signals in predetermined rules, and displays the result of the processing on the display device 31. The ROM 32 stores programs for the process carried out by the CPU 30, and data used for the processing. The RAM 33 is used such that when the CPU 30 executes the process, the CPU writes necessary data into the RAM 33 and reads out necessary data therefrom. The contents of the RAM 33 are in part shown in FIG. 3. As shown, the RAM includes a ring buffer containing a group of pulse-amplitude storing registers Ai and a group of pulse wave propagation time storing registers Ti and its ring buffer full flag F1. Here, i=0, 1, 2, . . . N−1 (N: number of addresses of the ring buffer).

The operation of the patient monitoring apparatus will be described with reference to a flow chart shown in FIG. 4. To start a measurement, the CPU 30 initializes the registers, flag and the like (step S1); waits till an R wave appears in the electrocardiogram signal (ECG) output from the electrocardiogram measuring means 1 (step S2); when an R wave appears, it measures an amplitude of a pulse wave corresponding to an R wave of the previous complete beat in the ECG and stores the result of the measurement into the pulse-amplitude storing register Ai (step S3); measures a time interval from R wave of previous ECG to the occurrence of the pulse wave corresponding to the R wave of the previous complete beat in the ECG; and stores the result of the measurement into the pulse wave propagation time storing register Ti (S4). An example of the measurement when i=1 is shown in FIG. 5.

The CPU 30 judges whether or not the contents of the ring buffer full flag F1 is 1 (1=buffer full) (step S5), and if it is 1, it measures a ratio of the heart rate and the heart rate exclusive of the heart beats of wave deficits (step S6).

Figure 6:
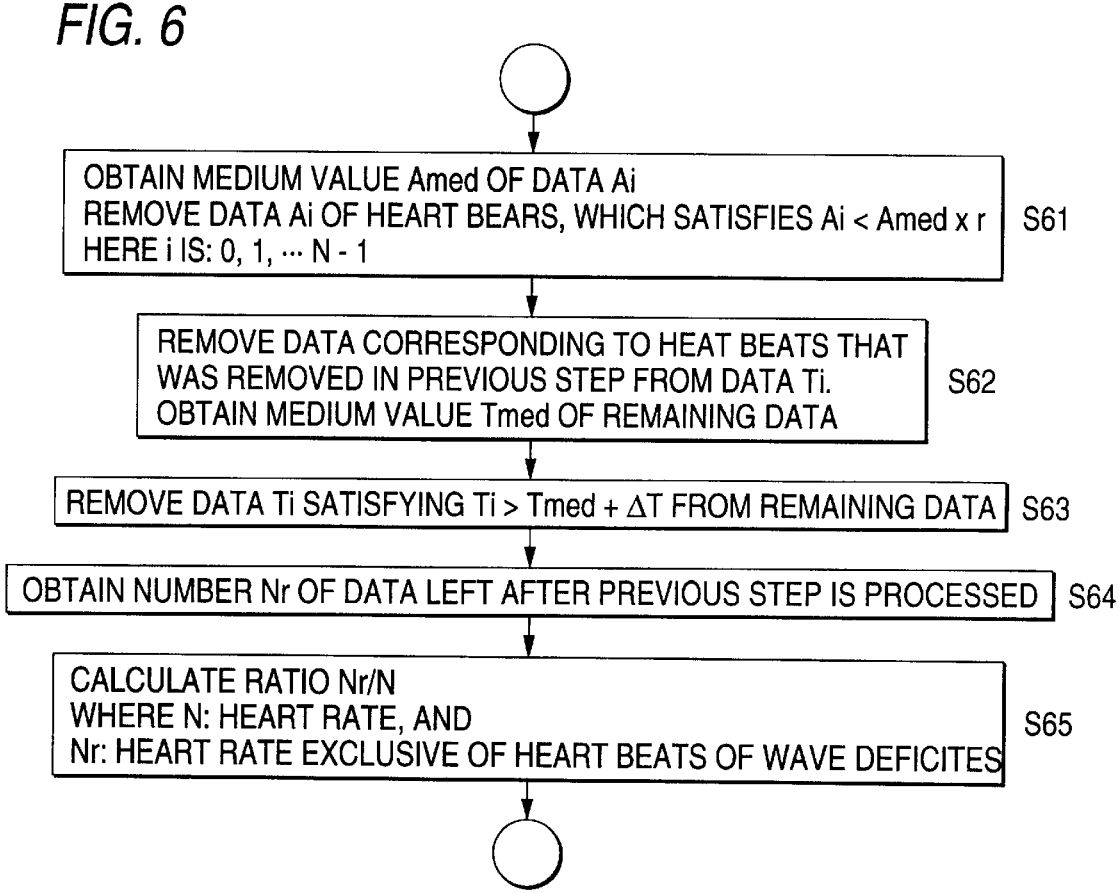
FIG. 6 is a flow chart showing the detail of the step S6 in the FIG. 4 flow chart.

The details of the step S6 will be described with reference to FIG. 6. The CPU 30 first obtains the medium value Amed of the data Ai stored in all the pulse-amplitude storing registers Ai, and removes the data Ai of heart beats, which satisfies Ai<Amed×r (step S61). Here, r is: 0<r<1. This value is a preset value for removing the heart beats of small amplitudes. Then, the CPU 30 removes the data corresponding to the heart beats that was removed in the step S61, from the data Ti stored in all the pulse wave propagation time storing registers Ti, and obtains a medium value Tmed of the remaining data (step S62). The CPU 30 removes the data Ti satisfying Ti>Tmed+ΔT (step S63). The heart beats corresponding to the data removed in the steps S61 and S62 are the heart beats of wave deficits. The CPU 30 obtains the number Nr of data left after the step S63 is processed (step S64). Subsequently, the CPU 30 computes a ratio Nr/N (where N : heart rate, and Nr : heart rate exclusive of the heart beats of the wave deficits), and displays the result of the computation on the screen of the display device 31 (step S65).

The heart beats whose amplitudes are small are removed in the step S61. The reason for this follows. In some of the wave deficits, the heart is little contracted, and therefore, some of the heart beats have extremely small amplitudes. In other words, the heat beats whose amplitudes are extremely small may be considered to be those of the pulse deficits.

The reason why the heart beats whose pulse wave propagation time is long is removed in the step S63 follows. In some of the pulse deficits, the heart contracts, but an insufficient amount of blood is fed to the ventricle. In such a case, the blood filling of the ventricle is insufficient, and therefore a preload on the heart is small, so that a contraction force of the heart does not increase as taught by Frank-Starling's theorem. Therefore, the pre-ejection period is long, and consequently the pulse wave propagation time is also long.

Further, same effect could be enjoyed by reversing the arrangement of Steps 61 and 63. Namely, in stead of steps 61 to steps 63, The CPU 30 obtains the medium value Tmed of data Ti stored in all the pulse wave propagation time storing registers Ti, and removes the data satisfying Ti>Tmed+ΔT'. Next, the CPU removes the data corresponding to the heart beats that was removed in step S61', from the data Ai stored in all the pulse-amplitude storing registers Ai, and obtains a medium value Amed of the remaining data. Next, it is applicable for removing data Ai satisfying Ai>Amed×r' from remaining dataAi after proceeding step S62'. After these steps, the process is the same as described before.

A case where a wave deficit occurs at the heart beat b1 is illustrated in FIG. 5. In this case, the amplitude A1 of the pulse wave is: A1<Amed×r (or the pulse wave propagation time Ti is: Ti<Tmed+ΔT), and the data of that beat is removed.

Following the step S6, the CPU 30 resets the ring buffer full flag F1 to "0" (step S7) (FIG. 4), and then advances to the next step SB. In this step, the CPU 30 checks if i=N−1 (i: contents of a pointer to point to the address of the ring buffer).

If not i=N−1, the CPU 30 adds 1 to the pointer contents (step S9), and returns to the step S2. If i=N−1, the CPU 30 resets the pointer contents i to 0 (step S10), sets the contents of the ring buffer full flag F1 to 1 (step S11), and returns to the step S2.

Figure 1:
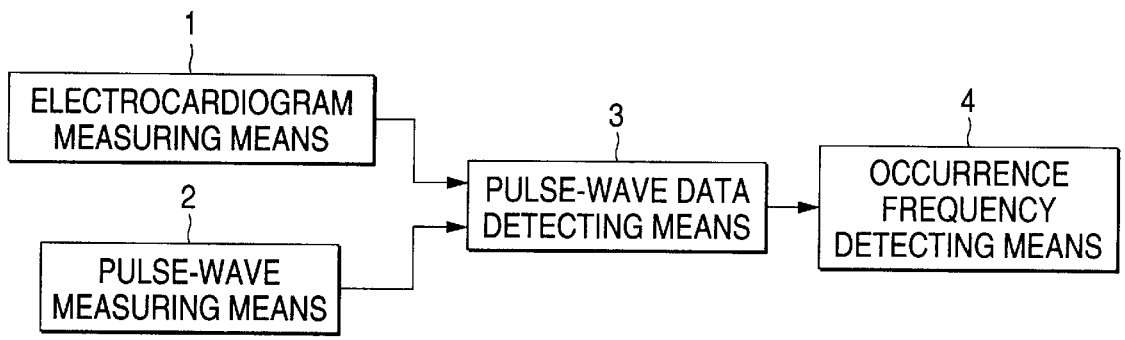
FIG. 1 is a block diagram showing the conceptual arrangement of a patient monitoring apparatus constructed according to the present invention.
Figure 4:
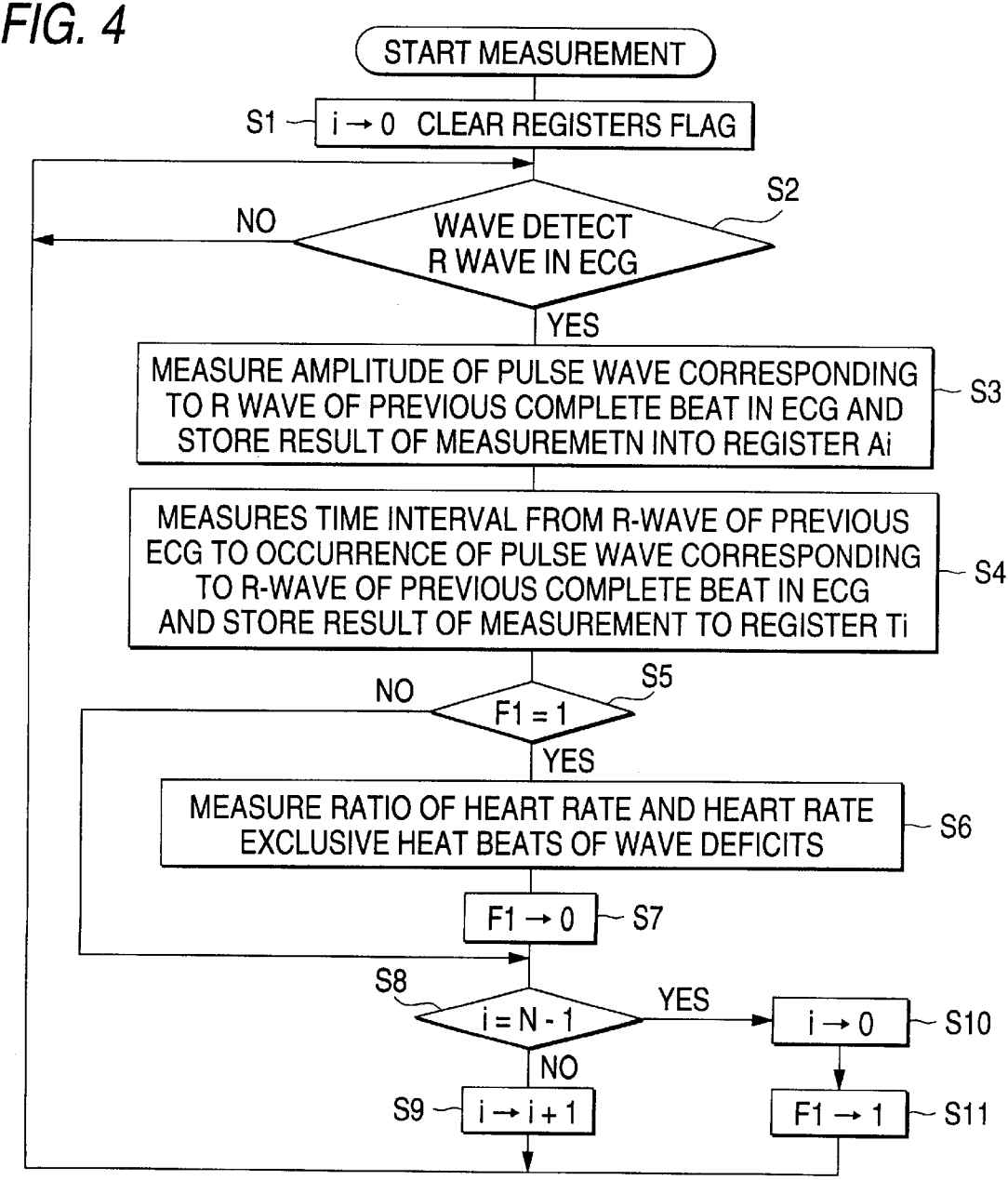
FIG. 4 is a flow chart showing an operation of the patient monitoring apparatus shown in FIGS. 1 and 2.
Figure 5:
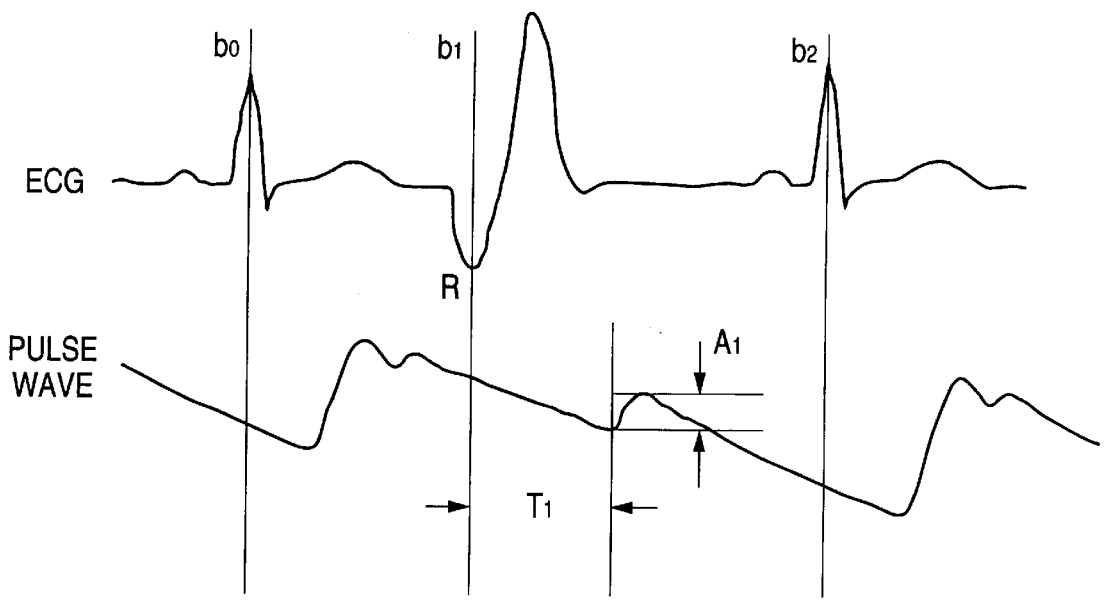
FIG. 5 is a waveform diagram showing an electrocardiogram and a pulse wave signal, processed by the FIGS. 1 and 2 apparatus.

The processings of the steps Si to S4 and S8 to S10 in FIG.4, carried by the CPU 30, correspond to the pulse wave data detecting means 3 in FIG. 1; and the processings of the steps S5 to S7, and S11 (FIG. 4) correspond to the occurrence-frequency detecting means 4 (FIG. 1).

In the present embodiment, r=0.1, and ΔT=30 msec. Further, the ratio of Nr/N is displayed in the embodiment. In an alternative, this ratio is compared with a preset value (=50% in this embodiment), and if it exceeds the preset value, it is judged that the heart contraction is abnormal, and produces an alarm sound.

In the embodiment, the ratio of Nr/N is obtained every time all the data about the pulse waves of an N number of heart beats are rewritten (FIG. 4). If necessary, the step S7 in the FIG. 4 flow chart may be omitted. In this case, after the ring buffers are full, the ratio of Nr/N is obtained every time the data of one heart beat. The monitoring of the heart contractions is more exact.

In the description thus far made, the pulse deficit is detected and then the heart contractions are monitored on the basis of the detection result. However, the apparatus, of this invention like the normal monitoring apparatus, is capable of displaying electrocardiograms and pulse wave signals by use of the display device 31. A no-invasive blood pressure measuring device may be attached to the patient monitoring apparatus of the invention. When a heart contraction is abnormal, the blood pressure monitoring device is operated to quickly check a blood pressure at that time.

As described above, to detect the pulse deficit, both the amplitude of pulse wave and the pulse wave propagation time are used. Therefore, the pulse deficit detection is more exact.

In the embodiment mentioned above, the amplitude of pulse wave is compared with a preset value, and the pulse wave propagation time is also compared with a preset value. A pulse deficit is detected on the basis of the comparisons the amplitude of pulse wave and pulse wave propagation time with the preset values, respectively, and the calculation of a ratio of the heart rate and the heart rate exclusive of the heart beats of pulse deficits is executed. If necessary, the heart rate may be compared with the pulse wave propagation time in their variances. If a variance ratio of them exceeds a predetermined value, it is judged that the heart contraction is abnormal.

According to the present invention, the patient monitoring apparatus is constructed incorporating the same thereinto to monitor changes in the heart contractions in a non-invasive manner. To detect changes in the heart contractions, the electrocardiograms and pulse signals, usually used for patient monitoring, are used. Therefore, there is no need of using specially designed detecting means. This leads to construction simplification of the apparatus.

According to the present invention, the amplitudes of pulse waves are additionally used for detecting changes in the heart contractions. An exact detection is secured.

What is claimed is:

1. An apparatus for non-invasive heart monitoring comprising:

electrocardiogram measuring means for measuring electrocardiograms;

pulse wave measuring means for measuring pulse waves;

pulse wave data detecting means for detecting at least a pulse wave propagation time by use of electrocardiogram information measured by said electrocardiogram measuring means and pulse wave signals measured by said pulse wave measuring means; and occurrence-frequency detecting means for determining a frequency of occurrence of a pulse deficit of a heart by use of pulse wave data detected by said pulse wave data detecting means.

2. The apparatus for non-invasive heart monitoring according to claim 1, wherein said pulse wave data detecting means also detects amplitudes of pulse waves measured by said pulse wave measuring means.

3. The apparatus for non-invasive heart monitoring according to claim 2, wherein said occurrence-frequency detecting means determines the frequency of occurrence of said pulse deficit by selecting pulse wave data having pulse wave propagation time greater than a predetermined period and pulse wave data having said amplitudes of pulse waves within a predetermined amplitude range.

4. The apparatus for non-invasive heart monitoring according to claim 1, wherein said occurrence-frequency detecting means determines said frequency of occurrence of said pulse deficit by selecting data from said pulse wave data having said pulse wave propagation time greater than a predetermined period.

5. A method for non-invasive heart monitoring, comprising the steps of:

measuring electrocardiograms of a patient;

measuring pulse waves of said patient;

detecting at least a pulse wave propagation time by use of measured electrocardiogram and pulse wave signals;

detecting amplitudes of pulse waves from the measured pulse wave signals;

storing the pulse wave propagation time and the amplitudes of measured pulse waves which are synchronized as a related data;

selecting data from the related data having pulse wave propagation time greater than a predetermined time period; and determining a frequency of occurrence of a pulse deficit of a heart from the selected data.

6. The method for non-invasive heart monitoring as in claim 5, wherein selecting data further includes:

narrowing selected data with data having amplitudes within a predetermined range.

7. A method for non-invasive heart monitoring, comprising the steps of:

measuring electrocardiograms of a patient;

measuring pulse waves of said patient;

detecting at least a pulse wave propagation time from the measured electrocardiogram and pulse wave signals;

detecting amplitudes of the pulse waves from the measured pulse wave signals;

storing the pulse wave propagation time and the amplitudes of the measured pulse waves which are synchronized as a related data;

selecting data having amplitudes of the pulse wave within a predetermined range from the related data; and determining a frequency of occurrence of a pulse deficit of a heart from the selected data.

8. The method for non-invasive heart monitoring as in claim 7, wherein selecting data further includes:

narrowing selected data with data having pulse wave propagation time greater than a predetermined time period.

9. The method for non-invasive heart monitoring as in claim 6, further comprising the step of:

calculating an occurrence ratio ($N_r/N$) where (N) is a patient heart rate and ($N_r$) is a heart rate exclusive of heart beats with pulse deficits.

10. The method for non-invasive heart monitoring as in claim 8, further comprising the step of:

calculating an occurrence ratio ($N_r/N$) where (N) is a patient heart rate and ($N_r$) is a heart rate exclusive of heart beats with pulse deficits.

11. An apparatus for non-invasive heart monitoring comprising:

an electrocardiogram for measuring a patient electrocardiogram signal;

a pulse wave measuring means for measuring a patient pulse wave signal;

a computer means receiving the measured signals from said electrocardiogram and said pulse wave measuring means, said computer means calculating and storing a pulse wave propagation time data and a pulse wave amplitude data, said computer means determining a frequency of occurrence of a pulse deficit of a heart by selecting said pulse wave propagation time data and said pulse wave amplitude data within a predetermined range of propagation time and amplitude values.

12. The apparatus for non-invasive heart monitoring as in claim 11, further comprising:

a display means for continuously displaying said patient electrocardiogram signal, said patient pulse wave signal, and the frequency of occurrence of said pulse deficit, said frequency of occurrence of said pulse deficit being displayed as a ratio ($N_r/N$), where N is a heart rate of a patient, and $N_r$ is a heart rate of a patient exclusive of heartbeats with pulse deficits.

* * * * *